United States Patent [19]

Mead et al.

[11] 4,124,300

[45] Nov. 7, 1978

[54] METHOD FOR AUTOMATIC FABRIC INSPECTION

[75] Inventors: Donald C. Mead, Granada Hills; Harvey L. Kasdan, Van Nuys, both of Calif.; Jordan L. Dorrity, Greenwood, S.C.

[73] Assignee: Greenwood Mills, Inc., Greenwood, S.C.

[21] Appl. No.: 660,252

[22] Filed: Feb. 23, 1976

[51] Int. Cl.$^2$ .................................................. G01N 21/30
[52] U.S. Cl. ................................... 356/429; 250/571; 356/357; 356/238
[58] Field of Search ............... 356/199, 200, 238, 111; 250/571, 572

[56] References Cited

U.S. PATENT DOCUMENTS

| 3,633,037 | 1/1972 | Langenbeck | 356/199 |
|---|---|---|---|
| 3,659,950 | 5/1972 | Troll et al. | 356/200 |
| 3,709,610 | 1/1973 | Kruegle | 356/111 |
| 3,783,296 | 4/1972 | Blevins | 356/111 |
| 3,797,939 | 3/1974 | Pryor | 356/111 |
| 3,937,580 | 2/1976 | Kasdan | 350/550 |
| 4,009,965 | 3/1977 | Pryor | 356/111 |

*Primary Examiner*—John K. Corbin
*Assistant Examiner*—R. A. Rosenberger
*Attorney, Agent, or Firm*—Cushman, Darby & Cushman

[57] ABSTRACT

Fabric such as textile material is automatically inspected at high speed by diffraction of light techniques. The fabric is moved through a plane and irradiated with monochromatic light of given cross sectional area sufficient to encompass a large number of warp and fillings making up the fabric. The diffraction pattern developed after the beam has passed through the fabric is detected and various regions of this diffraction pattern are processed to provide data indicative of the quality of the fabric. The major regions involved in the diffraction pattern include the developed central lobe and first order side lobes along orthogonal axes normal to the directions of the warps and filling threads of the fabric.

28 Claims, 5 Drawing Figures

METHOD FOR AUTOMATIC FABRIC INSPECTION

This invention relates to an improved method for automatic fabric inspection particularly useful in the textile industry.

BACKGROUND OF THE INVENTION

It is conventional practice for quality control purposes to inspect fabric manufactured in textile mills.

At the present time, there are two basic techniques for such inspection. First, light is transmitted through the fabric and the intensity of the light measured. Variations in the intensity will indicate variations in density of the fabric material. Second, a reflective technique is employed wherein fabric is irradiated with light and the reflected light therefrom is analyzed.

Another technique known in the art for analyzing various materials is that of utilizing monochromatic light and developing diffraction patterns. For example, a single wire filament can be so analyzed as to size and form by irradiating the filaments with monochromatic light and analyzing the developed diffraction pattern. See, e.g., U.S. Pat. No. 3,659,950 issued May 2, 1972. However, so far as we are aware, no feasible technique has been developed prior to the present invention for a rapid analysis of fabric utilizing diffraction pattern techniques.

BRIEF DESCRIPTION OF THE PRESENT INVENTION

With the foregoing in mind, the present invention contemplates an improved method for fabric inspection particularly applicable to quality control of fabric manufactured in textile mills.

More particularly, we have discovered that diffraction pattern analysis techniques may be utilized in the high speed inspection of fabric from mills by the irradiation of the fabric with a monochromatic light beam of a given cross-sectional area sufficient to encompass a large number of the warp and fillings making up the fabric. In this respect, our method differs from known methods of diffraction analysis of materials.

In addition to the basic step of encompassing a large number of warp and filling threads, the developed diffraction pattern is in the form of a time sequential pattern in a single output plane. Thus, the fabric is caused to move through a given plane while being irradiated with the monochromatic light and the sequential developed pattern at the output plane is continuously analyzed.

Many different types of defects in fabric can readily be detected by processing various regions in the output plane of the diffraction pattern and the fabric graded in accordance with the output data furnished by this processing.

BRIEF DESCRIPTION OF THE DRAWINGS

A better understanding of the method of this invention will be had by referring to the accompanying drawings in which.

DETAILED DESCRIPTION OF THE INVENTION

Figure 1:
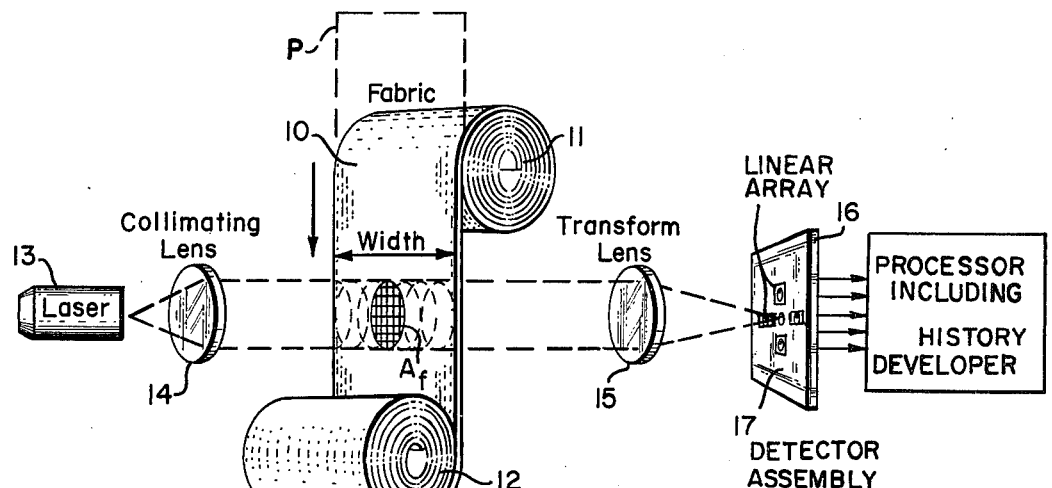
FIG. 1 is a highly schematic perspective view of the basic components for automatic fabric inspection in accord with this invention.

Referring first to FIG. 1, there is shown typical fabric material 10 from a textile mill which is caused to move downwardly as indicated by the arrow in a vertical plane P. Any suitable fabric transport system can be provided such as a supply roll 11 and take-up roll 12 for the fabric 10.

The basic components for carrying out the method include a monochromatic light source such as a laser 13 for irradiating the fabric with a collimated beam formed by a collimating lens 14. The irradiated area is indicated at $A_f$ and is of sufficient cross-sectional area to encompass a large number of the warps and fillings of the fabric.

Typical fabrics may have from 40 to 100 threads (that is, warps or fillings) per inch. Thus, the expression "large number" as used herein would typically be from 40 to 100 or more threads per inch. However, the technique is workable for a number as low as 25 but in most instances, the number of warps or fillings per inch would exceed this minimum number. The diameter of the beam from the collimating lens 14, in turn, may be between 1 and 2 inches.

As is evident from FIG. 1, the monochromatic light beam is directed towards one side of the fabric 10 preferably in a direction substantially normal to the plane of the fabric. The light beam after passing to the other side of the fabric is focussed by transform lens 15 onto a detector 16, a diffraction pattern being developed in a single output plane 17.

In order that the entire area of the fabric 10 be inspected, the area $A_f$ is scanned across the width of the fabric as indicated by the phantom lines at the same time that the fabric 10 is moving downwardly. Thus, the pattern developed in the plane 17 of the detector will be a time sequential pattern for all of the successive areas irradiated by the monochromatic light beam.

Figure 2:
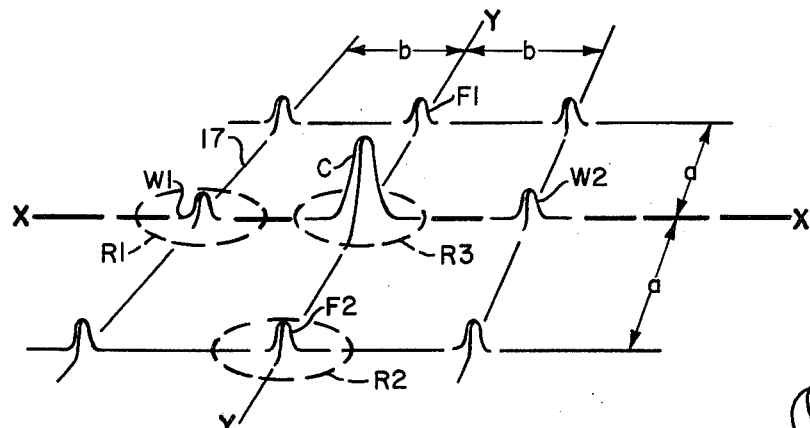
FIG. 2 is a perspective view of the developed time sequential diffraction pattern at the output plane of the detector of FIG. 1.

FIG. 2 schematically illustrates the developed diffraction pattern wherein there is provided a central lobe C with various first order side lobes. The side lobes of importance in this diffraction pattern are those lying on axes X—X and Y—Y which axes are oriented in directions normal to the directions of the warp and filling threads of the fabric, respectively.

With respect to the foregoing, if the warp constitutes the vertical threads in the fabric as viewed in FIG. 1 and the filling the horizontal threads, the side lobes W1 and W2 along the X—X axis of FIG. 2 results from the warps whereas the side lobes F-1 and F-2 along the Y—Y axis result from the fills. As stated, it is principally these first order side lobes along the X—X and Y—Y axes as described which are important along with the central lobe in providing an indication of the overall quality of the fabric.

The processing of the diffraction pattern to grade the fabric involves collapsing each of the lobes into a sheet of energy by an anamorphic lens system. Each of these sheets of energy (or one dimensional side lobe pattern) is then processed by its own individual photo detector array which converts the light intensity into electrical form. Each of the sequential electronic signals is then processed to make good v. defective decisions.

Thus, still referring to FIG. 2, various regions of the diffraction pattern are individually processed, typical regions being indicated within the broken line enclosures R1, R2 and R3.

Figure 3:
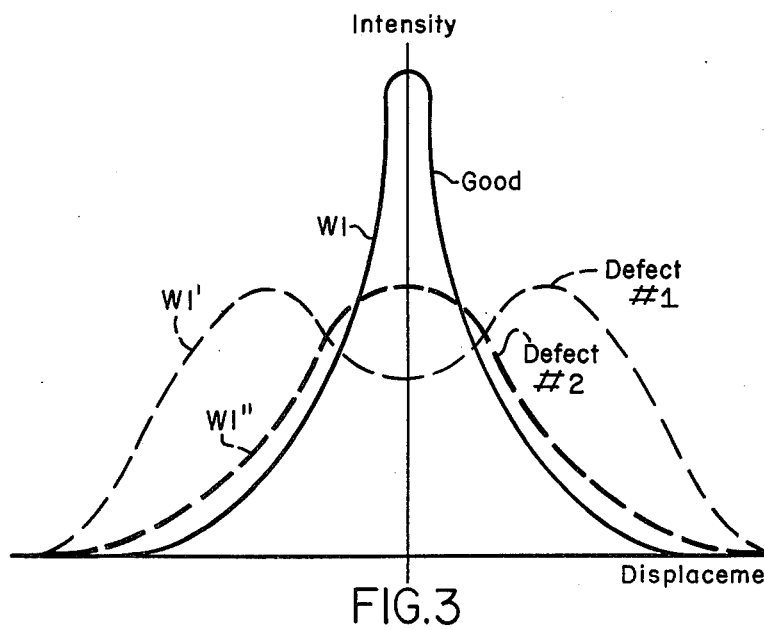
FIG. 3 is an enlarged view of one of the side lobes of the diffraction pattern of FIG. 2.
Figure 4:
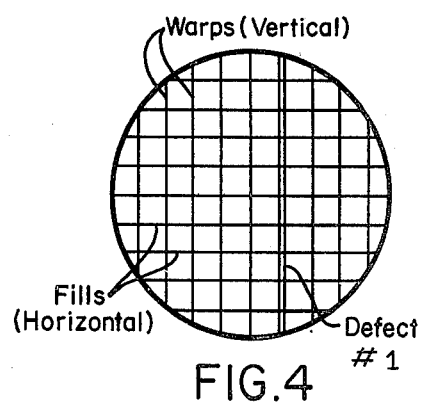
FIG. 4 is a greatly magnified view of a fabric area under analysis illustrative of a first type of defect; and, FIG. 5 is a view similar to FIG. 4 illustrating a second type of fabric defect.

Considering first, by way of example, the side lobe W1 and the region R1 there is illustrated in FIG. 3 a cross section of the lobe in solid line which results when the fabric is "good." In the event there is a defect in the warp, the height and shape of this lobe is changed usually by a lowering of the side lobe peak and a broadening of its overall shape. A specific defect is illustrated in FIG. 4, wherein there is a double thread (two closely spaced warp) designated defect #1. Referring back to FIG. 3, the solid line lobe would degenerate into a size and shape indicated at W1'. This defect is referred to as a "double thread" defect.

Figure 5:
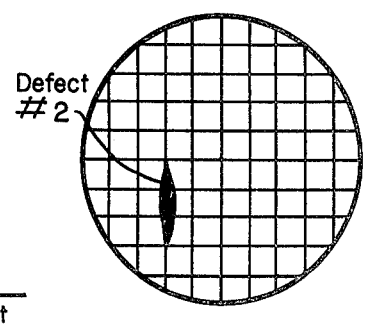

A second type of defect is illustrated in FIG. 5 and is referred to in the art as a "slub." This defect is indicated as defect #2 and might result from foreign material on one of the warp.

Referring back again to FIG. 3, such a defect would typically result in a degeneration of the "good" solid line curve for the lobe to the dashed curved W1".

It will be evident from the foregoing, that by simply comparing the heights and shapes of the side lobes to given references, the desired output data can be obtained and a grade count accorded the particular cross sectional area of the fabric being inspected. An important one of the given references for comparison purposes is that of the height and shape of the central lobe. This central lobe in itself provides valuable information as to major defects since its intensity will vary with changes in density of the overall fabric material. In addition, however, by utilizing the central lobe as a comparison reference for the side lobes, the analysis of the side lobes will be essentially independent of changes in the transmissivity of the fabric.

The method of this invention also includes processing steps involving the comparing of the distances between the centroids of the side lobes with given references to determine spacing between the warps and between the fillings of the fabric. These distances are indicated by the small letters $a$ and $b$ in FIG. 2 and serve as an indication to enable the number of warps and the number of fillings per inch to be determined.

In the preferred method of this invention, the given references for comparison purposes are provided from the mean value of a history of amplitude and shape comparisons of the side lobes. For example, if the number of occurrences in any of the amplitude quantitization levels is further than $+$ or $-$ one standard deviation from its mean value, a decision of a defect would be made. Such histograms are preferably developed as noted, relative to the central lobe so that the decisions can be made independently of the fabric transmissivity.

Further, in the preferred embodiment of this invention a statistical history of the height and shapes of the side lobes is formed in an adaptive manner, the history for a current decision being related only to the last few samples tested.

From the foregoing, it will be appreciated that not only are individual sequentially graded local areas of the fabric through which the beam passes carried out, but in addition, the individual grades of such local areas over a given large area of the fabric can be totalled and an overall grade assigned to a large area as to its quality.

The comparisons of the shapes and heights of the side lobes with given references can actually be carried out by simply observing the developed diffraction patterns on a screen positioned in front of the detector 16 of FIG. 1. In this case the pattern is visually observed and compared to the pattern developed by a "good" fabric. Photographs can be taken of the pattern on the screen and compared with previous photographs.

Preferably, however, the first order side lobes are squeezed by a lens and detected in a photo-diode linear array. One such type of diode detector is shown and described in U.S. Pat. No. 3,937,580 issued Feb. 10, 1976 to Harvey Lee Kasdan one of the co-inventors in this application. Another type of photo-detector array which could serve to process the diffraction pattern of this invention is shown and described in U.S. Pat. No. 3,689,772 issued Sept. 5, 1972. In this latter respect, the basic method of fabric inspection in accord with this invention has been carried out using a photo-detector as shown in U.S. Pat. No. 3,689,772 with portions masked off to provide a linear array so that side lobes along either the X—X or Y—Y axis could be individually analyzed by appropriately orienting the unmasked portion of the array parallel to the particular axis under investigation.

From the foregoing description, it will be evident that the present invention has thus provided a greatly improved method for the rapid inspection and grading of fabric from textile mills and can be carried out in a manner to provide substantially more information as to the fabric quality than has been possible with prior art methods involving simple light transmissivity of the fabric or reflection characteristics from one side of the fabric.

What is claimed is:

1. A method of automatically inspecting fabric comprised of warp and filling threads to determine the quality of the fabric, including the steps of:
   (a) irradiating the fabric with a beam of monochromatic light of given cross-sectional area sufficient to encompass a large number of warp and filling threads for developing from said fabric a diffraction pattern having a central lobe and side lobes,
   (b) detecting at least a part of said diffraction pattern including detecting a predetermined number of said side lobes respectively by a corresponding number of linear arrays of photodetectors without using any reference diffraction pattern, and
   (c) individually analyzing each detected side lobe itself by processing only the outputs of the photodetector array corresponding to the respective detected side lobe being analyzed to provide data indicative of the quality of said fabric,
   said side lobes being along axes oriented in directions normal to said warp and filling threads respectively, and wherein said processing step includes the steps of comparing the height and shapes of said side lobes to given references to provide at least a part of said output data.

2. The method of claim 1, in which one of said given references constitutes the height and shape of said central lobe.

3. The method of claim 2, including the step of comparing the height and shape of said central lobe with a given standard to provide information indicative of major defects in said fabric.

4. The method of claim 1, in which at least some of said given references are provided from the mean value of a history of amplitude and shape comparisons of said side lobes.

5. The method of claim 1, in which said processing step includes the further steps of comparing the distance between centroids of the side lobes with given references to determine spacing between warp threads and between filling threads of said fabric to thereby enable the number of warps per inch and enable the number of fillings per inch to be determined.

6. A method as in claim 1 including moving the fabric in a given plane and grading the fabric in accordance with the said data furnished by said processing.

7. The method of claim 6, including the step of individually sequentially grading local areas of the fabric through which said beam passes.

8. The method of claim 7, including the steps of totalling the individual grades of local areas over a given large area of said fabric and assigning an overall grade to said large area as to quality based on said totalling.

9. The method of claim 1, in which said large number of warps and fillings is at least 25 per inch.

10. A method as in claim 1 wherein step (c) includes analyzing at least the intensity of at least one side lobe developed in said diffraction pattern.

11. A method as in claim 1 wherein step (c) includes analyzing at least the displacement of at least one side lobe developed in said diffraction pattern.

12. A method as in claim 1 wherein step (c) includes analyzing the intensity versus displacement relationship of at least one side lobe developed in said diffraction pattern.

13. A method as in claim 1 wherein said step (c) includes analyzing at least one side lobe relative to said central lobe.

14. A method as in claim 1 wherein said fabric is moved during at least steps (a) and (b) and step (c) includes analyzing at least one side lobe relative to said central lobe essentially independently of changes in transmissivity of said fabric due to its movement.

15. A method as in claim 1 wherein said processing includes comparing the distance between centroids of the side lobes with given references to determine spacing between warp threads and between filling threads of said fabric for determining the respective numbers of warps and fillings per unit of measurement.

16. A method as in claim 1 including moving the fabric in a given plane and wherein said step (c) includes comparing at least one aspect of at least one current lobe with a recent history of that aspect of similar lobes.

17. A method as in claim 16 wherein said recent history is a statistical history formed in an adaptive manner of the height and shapes of side lobes in the successive diffraction patterns developed in said plane during movement of said fabric, the history for a current lobe comparison being continuously updated and related only to a predetermined number of immediately preceding diffraction patterns.

18. A method as in claim 17 wherein each said side lobes of the respective pattern are related to develop a continuously updated history which is independent of changes in transmissivity of the fabric during its movement.

19. A method as in claim 1 wherein step (b) includes detecting at least one warp side lobe and at least one filling side lobe in said predetermined number of side lobes and step (c) includes analyzing both said warp and filling lobes by processing the outputs of the photodetector arrays for said warp and filling side lobes.

20. A method as in claim 19 wherein said step (b) includes detecting said central lobe by a photodetector and step (c) includes analyzing said central lobe by processing the output of said photodetector.

21. A method as in claim 1 wherein the developed diffraction pattern side lobes include two first order warp side lobes and two first order filling side lobes, all four of said warp and filling side lobes being detected in step (b) and analyzed in step (c).

22. A method as in claim 21 and further including detecting and analyzing said central lobe.

23. A method of automatically inspecting fabric comprised of warp and filling threads to determine the quality of the fabric, including the steps of:
  (a) irradiating the fabric with a beam of monochromatic light of given cross-sectional area sufficient to encompass a large number of warp and filling threads for developing from said fabric a diffraction pattern having a central lobe and side lobes,
  (b) detecting at least part of said diffraction pattern including detecting a predetermined number of said side lobes by a respective plurality of linearly arrayed photodetectors without using any reference diffraction pattern, and
  (c) individually analyzing each detected side lobe itself by processing only the outputs of that plurality of photodetectors employed in step (b) to detect the respective side lobe being analyzed to provide data indicative of the quality of said fabric,
  said side lobes being along axes oriented in directions normal to said warp and filling threads respectively, and wherein said processing step includes the steps of comparing the height and shapes of said side lobes to given references to provide at least a part of said output data.

24. A method as in claim 23 including moving the fabric in a given plane and grading the fabric in accordance with the said data furnished by said processing.

25. A method as in claim 23 wherein step (b) includes detecting at least one warp side lobe and at least one filling side lobe in said predetermined number of side lobes and step (c) includes analyzing both said warp and filling lobes by processing the outputs of the photodetector arrays for said warp and filling side lobes.

26. A method as in claim 25 wherein said step (b) includes detecting said central lobe by a photodetector and step (c) includes analyzing said central lobe by processing the output of said photodetector.

27. A method as in claim 23 wherein the developed diffraction pattern side lobes include two first order warp side lobes and two first order filling side lobes, all four of said warp and filling side lobes being detected in step (b) and analyzed in step (c).

28. A method as in claim 27 and further including detecting and analyzing said central lobe.

* * * * *